(12) United States Patent
McNair (10) Patent No.: US 9,084,585 B1
(45) Date of Patent: Jul. 21, 2015

(54) SYSTEM AND METHOD TO CLASSIFY LEFT VENTRICULAR AND MITRAL VALVE FUNCTION

(75) Inventor: Douglas S. McNair, Leawood, KS (US)

(73) Assignee: CERNER INNOVATION, INC., Kansas City, KS (US)

( * ) Notice: Subject to any disclaimer, the term of this patent is extended or adjusted under 35 U.S.C. 154(b) by 953 days.

(21) Appl. No.: 13/267,616

(22) Filed: Oct. 6, 2011

(51) Int. Cl.
| A61B 5/02 | (2006.01) |
| A61B 5/00 | (2006.01) |
| A61B 5/021 | (2006.01) |
| A61B 5/0295 | (2006.01) |
| A61B 5/053 | (2006.01) |

(52) U.S. Cl.
CPC ............... *A61B 5/7239* (2013.01); *A61B 5/021* (2013.01); *A61B 5/02028* (2013.01); *A61B 5/0295* (2013.01); *A61B 5/0535* (2013.01); *A61B 5/7264* (2013.01); *A61B 5/6824* (2013.01)

(58) Field of Classification Search
CPC ........ A61B 5/053; A61B 5/0295; A61B 5/02; A61B 5/021; A61B 5/02028; A61B 5/029; A61B 5/7235; A61B 5/7239; A61B 5/7246; A61B 5/0535
USPC .................................. 600/481, 485, 504, 506
See application file for complete search history.

(56) References Cited

U.S. PATENT DOCUMENTS

| 5,025,795 | A  * | 6/1991 | Kunig ........................... 600/526 |
| 7,261,697 | B2 | 8/2007 | Berstein |
| 8,595,159 | B2 * | 11/2013 | McNair .......................... 706/12 |
| 2005/0283088 | A1 * | 12/2005 | Bernstein ...................... 600/506 |
| 2009/0259132 | A1 * | 10/2009 | Bernstein ...................... 600/506 |
| 2010/0030293 | A1 * | 2/2010 | Sarkar et al. .................... 607/18 |
| 2012/0095300 | A1 * | 4/2012 | McNair .......................... 600/300 |

OTHER PUBLICATIONS

Robert T. Clemen and Terence Reilly; Correlations and Copulas for Decision and Risk Analysis; Mar. 1997; 32 pages.

* cited by examiner

*Primary Examiner* — Navin Natnithithadha
*Assistant Examiner* — Meredith Weare
(74) *Attorney, Agent, or Firm* — Shook, Hardy & Bacon L.L.P.

(57) ABSTRACT

Methods, systems, and computer storage media are provided for determining whether a patient suffers from one or both of a recent deterioration in left ventricular function and a recent deterioration in mitral valve function. Transbrachial impedance velocimetry data and arterial pressure waveform data is received from a particular patient at a plurality of timepoints. An extent of deterioration is determined using a copula analysis of the patient data, and a statistical norm is determined for the patient's left ventricular function and mitral valve function. A current data value is received from the patient, including current transbrachial impedance velocimetry data and arterial pressure waveform data. The current data value is compared to the patient's statistical norm to determine whether the patient suffers from a recent deterioration in left ventricular function and/or mitral valve function.

18 Claims, 5 Drawing Sheets

SYSTEM AND METHOD TO CLASSIFY LEFT VENTRICULAR AND MITRAL VALVE FUNCTION

BACKGROUND

Efforts to enhance the continuity of patient care and minimize unnecessary hospitalization costs have increased the demand for patient monitoring, in both ambulatory contexts and acute-care hospital settings. Continuous patient monitoring that is both accurate and convenient is desired to assess the severity of a medical condition before it escalates to a level that is less responsive to intervention, or requires more invasive treatment. Such monitoring may be used to identify certain abnormalities that precede clinically significant and life-threatening deterioration/decompensation of a patient's health status. For example, monitoring may be used to determine if a patient is experiencing a clinically significant deterioration in left ventricular function and/or mitral valve function. However, traditional monitoring methods used to detect left ventricular dysfunction (LVD) and mitral valve regurgitation (MR) often produce false-positive and false-negative results, and are unduly invasive, costly, and time-consuming. Thus, clinicians are not able to easily ascertain the emergence of significant changes in LVD and/or worsening of MR for the purposes of prevention and early identification.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to determining whether a patient suffers from one or both of a recent deterioration in left ventricular function and a recent deterioration in mitral valve function. A patient monitor is used to retrieve transbrachial impedance velocimetry data and arterial pressure waveform data. In particular, the patient is monitored and data is collected at multiple intervals during the systolic phase of the cardiac cycle. Patient data may also be retrieved at a plurality of timepoints, such as serially collected data retrieved during continuous patient monitoring. Computation of a statistical copula from the patient data provides an indication of a patient's status with respect to LVD and MR, including a statistical norm for the patient's levels of left ventricular function and mitral valve function. Additionally, a current data value may be used to determine a patient's current LVD and MR status.

Accordingly, in one aspect, the present invention is directed to one or more computer storage media storing computer-useable instructions that, when executed by one or more computing devices, cause the one or more computing devices to perform a method for classifying one or both of left ventricular function and mitral valve function. The method comprises: receiving data from a particular patient at a plurality of timepoints, wherein the data comprises transbrachial impedance velocimetry data collected from the patient at the plurality of timepoints and arterial pressure waveform data collected from the patient at the plurality of timepoints; determining an extent of deterioration at each of the plurality of timepoints of one or both of left ventricular function and mitral valve function based on the transbrachial impedance velocimetry data and the arterial pressure waveform data; determining a statistical norm for the particular patient based on the determined extent of deterioration; receiving a current data value from the patient at a current timepoint, wherein the current data value comprises transbrachial impedance velocimetry data collected from the patient at the current timepoint and arterial pressure waveform data collected from the patient at the current timepoint; and determining whether the patient suffers from one or both of a recent deterioration in left ventricular function and a recent deterioration in mitral valve function, wherein determining whether the patient suffers from a recent deterioration is based on the statistical norm for the patient and the current data value.

In another aspect, the present invention is directed to a method for classifying one or both of left ventricular function and mitral valve function. The method comprises: receiving medical monitoring data from a particular patient, the medical monitoring data comprising transbrachial impedance velocimetry data and arterial pressure waveform data, wherein the medical monitoring data is received at a plurality of timepoints; determining a statistical norm for the particular patient based on the medical monitoring data; receiving a current data value from the particular patient, the current data value comprising transbrachial impedance velocimetry data and arterial pressure waveform data; based on the determined statistical norm and the received current data value, determining whether the patient suffers from one or both of a recent deterioration in left ventricular function and a recent deterioration in mitral valve function; and generating a report indicating whether the patient suffers from one or both of a recent deterioration in left ventricular function and a recent deterioration in mitral valve function.

In yet another aspect, the present invention is directed to one or more computer storage media storing computer-useable instructions that, when executed by one or more computing devices, cause the one or more computing devices to perform a method for classifying left ventricular function and mitral valve function. The method comprises: receiving data from a particular patient at a plurality of timepoints, wherein the data comprises transbrachial impedance velocimetry data collected from the patient at the plurality of timepoints and arterial pressure waveform data collected from the patient at the plurality of timepoints; determining a statistical copula between a second derivative of square-root-transformed patient-calibrated transbrachial electrical impedance velocimetry waveform timeseries $d^2sqrt(Z(t)/Z_0)/dt^2$ and a first derivative of arterial blood pressure waveform timeseries dP/dt during a first and second interval at each of the plurality of timepoints; determining an extent of deterioration at each of the plurality of timepoints of left ventricular function based on the statistical copula determined during the first and second intervals; determining a statistical copula between a second derivative of square-root-transformed patient-calibrated transbrachial electrical impedance velocimetry waveform timeseries $d^2sqrt(Z(t)/Z_0)/dt^2$ and a first derivative of arterial blood pressure waveform timeseries dP/dt during a third interval at each of the plurality of timepoints; determining an extent of deterioration at each of the plurality of timepoints of mitral valve function based on the statistical copula determined during the third interval; determining a statistical norm for the particular patient based on the determined extent of deterioration of left ventricular function and the determined extent of deterioration of mitral valve function; receiving a current data value from the patient at a current timepoint, wherein the current data value comprises transbrachial impedance velocimetry data collected from the patient at the current timepoint and arterial pressure waveform data collected from the patient at the current timepoint; determining a statistical copula between a second derivative of square-roottransformed patient-calibrated transbrachial electrical impedance velocimetry waveform timeseries $d^2sqrt(Z(t)/Z_0)/dt^2$ and a first derivative of arterial blood pressure waveform timeseries dP/dt during a first and second interval at the current timepoint; determining an extent of deterioration at the current timepoint of left ventricular function based on the statistical copula determined during the first and second intervals; determining a statistical copula between a second derivative of square-root-transformed patient-calibrated transbrachial electrical impedance velocimetry waveform timeseries $d^2sqrt(Z(t)/Z_0)/dt^2$ and a first derivative of arterial blood pressure waveform timeseries dP/dt during a third interval at the current timepoint; determining an extent of deterioration at the current timepoint of mitral valve function based on the statistical copula determined during the third interval; and determining whether the patient suffers from one or both of a recent deterioration in left ventricular function and a recent deterioration in mitral valve function, wherein determining whether the patient suffers from a recent deterioration is based on the statistical norm, the determined extent of deterioration of left ventricular function at the current timepoint, and the determined extent of deterioration of mitral valve function at the current timepoint.

BRIEF DESCRIPTION OF THE DRAWINGS

The present invention is described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention relate to determining whether a patient suffers from one or both of a recent deterioration in left ventricular function and a recent deterioration in mitral valve function. A patient monitor is used to retrieve transbrachial impedance velocimetry data and arterial pressure waveform data. In particular, the patient is monitored and data is collected at multiple intervals during the systolic phase of the cardiac cycle. Patient data may also be retrieved at a plurality of timepoints, such as serially collected data retrieved during continuous patient monitoring. Computation of a statistical copula from the patient data provides an indication of a patient's status with respect to LVD and MR, including a statistical norm for the patient's levels of left ventricular function and mitral valve function. Additionally, a current data value may be used to determine a patient's current LVD and MR status.

Having briefly described embodiments of the present invention, an exemplary operating environment suitable for use in implementing embodiments of the present invention is described below. Referring to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

Figure 1:
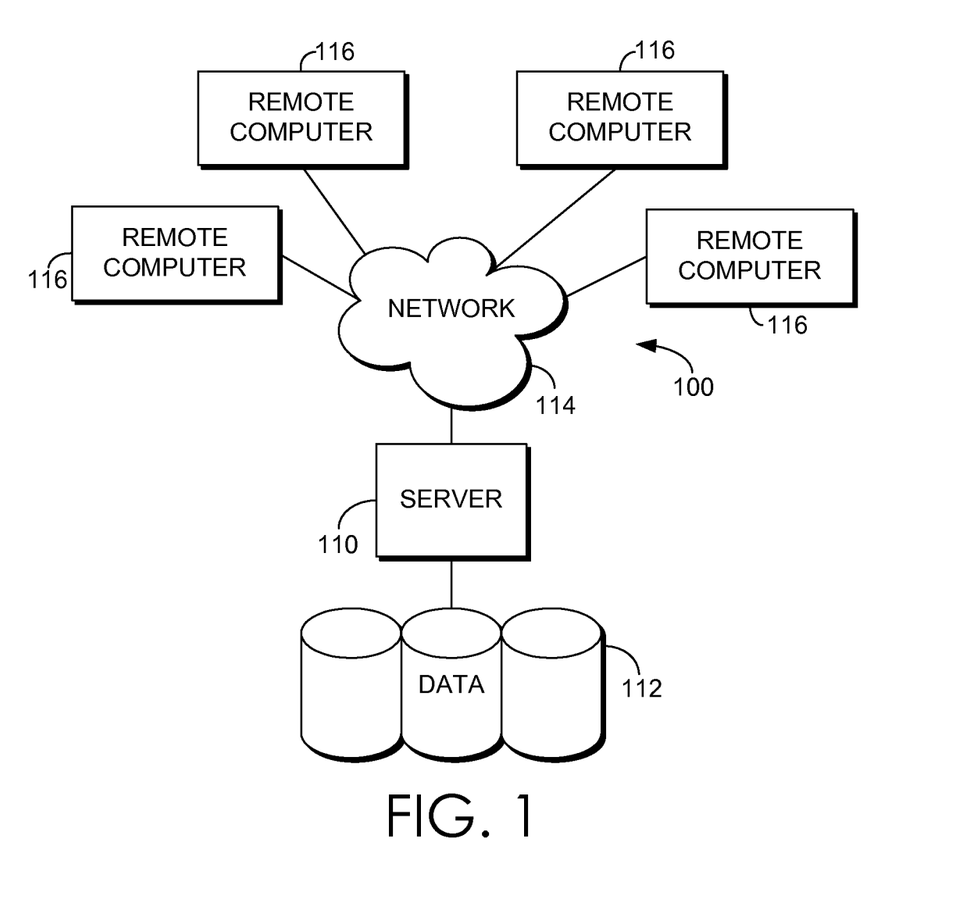
FIG. 1 is a block diagram of an exemplary computing environment suitable for use in implementing the present invention.

With continued reference to FIG. 1, the exemplary medical information computing system environment 100 includes a general purpose computing device in the form of a server 110. Components of the server 110 may include, without limitation, a processing unit, internal system memory, and a suitable system bus for coupling various system components, including database cluster 112, with the server 110. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 110 typically includes, or has access to, a variety of computer-readable media, for instance, database cluster 112. Computer-readable media can be any available media that may be accessed by server 110, and includes volatile and nonvolatile media, as well as removable and non-removable media. By way of example, and not limitation, computer-readable media may include computer storage media and communication media. Computer storage media may include, without limitation, volatile and nonvolatile media, as well as removable and nonremovable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 110. Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 112, provide storage of computer-readable instructions, data structures, program modules, and other data for the server 110.

The server 110 may operate in a computer network 114 using logical connections to one or more remote computers 116. In some embodiments, server 110 includes an adaptive multi-agent operating system, but it will be appreciated that server 110 may also take the form of an adaptive single agent system or a non-agent system. Server 110 may be a distributed computing system, a centralized computing system, a single computer such as a desktop or laptop computer or a networked computing system.

In some embodiments of our invention, server 110 is a multi-agent computer system with agents. In these embodiments, server 110 may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents based on beliefs, capabilities and choices that communicate via declarative messaging and use abstractions to allow for future adaptations and flexibility. An agent has its own thread of control which promotes the concept of autonomy. Additional information about the capabilities and functionality of agents and distributed multi-agent operating systems, as they relate to our invention, is provided in U.S. Provisional Patent Application No. 61/389,053, filed on Oct. 1, 2010, which is herein incorporated by reference in its entirety.

Remote computers 116 may be located at a variety of locations in a medical or research environment, for example, but not limited to, clinical laboratories, hospitals and other inpatient settings, veterinary environments, ambulatory settings, medical billing and financial offices, hospital administration settings, home healthcare environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 116 may also be physically located in nontraditional medical care environments so that the entire healthcare community may be capable of integration on the network. The remote computers 116 may be personal computers, servers, routers, network PCs, peer devices, other common network nodes, or the like, and may include some or all of the components described above in relation to the server 110. The devices can be personal digital assistants, mobile phones, portable music players, tablet computers, or other like devices.

Exemplary computer networks 114 may include, without limitation, local area networks (LANs) and/or wide area networks (WANs). Such networking environments are commonplace in offices, enterprise-wide computer networks, intranets, and the Internet. When utilized in a WAN networking environment, the server 110 may include a modem or other means for establishing communications over the WAN, such as the Internet. In a networked environment, program modules or portions thereof may be stored in the server 110, in the database cluster 112, or on any of the remote computers 116. For example, and not by way of limitation, various application programs may reside on the memory associated with any one or more of the remote computers 116. It will be appreciated by those of ordinary skill in the art that the network connections shown are exemplary and other means of establishing a communications link between the computers (e.g., server 110 and remote computers 116) may be utilized.

In operation, a user may enter commands and information into the server 110 or convey the commands and information to the server 110 via one or more of the remote computers 116 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 110. In addition to a monitor, the server 110 and/or remote computers 116 may include other peripheral output devices, such as speakers and a printer.

Although many other internal components of the server 110 and the remote computers 116 are not shown, those of ordinary skill in the art will appreciate that such components and their interconnection are well known. Accordingly, additional details concerning the internal construction of the server 110 and the remote computers 116 are not further disclosed herein.

Figure 2:
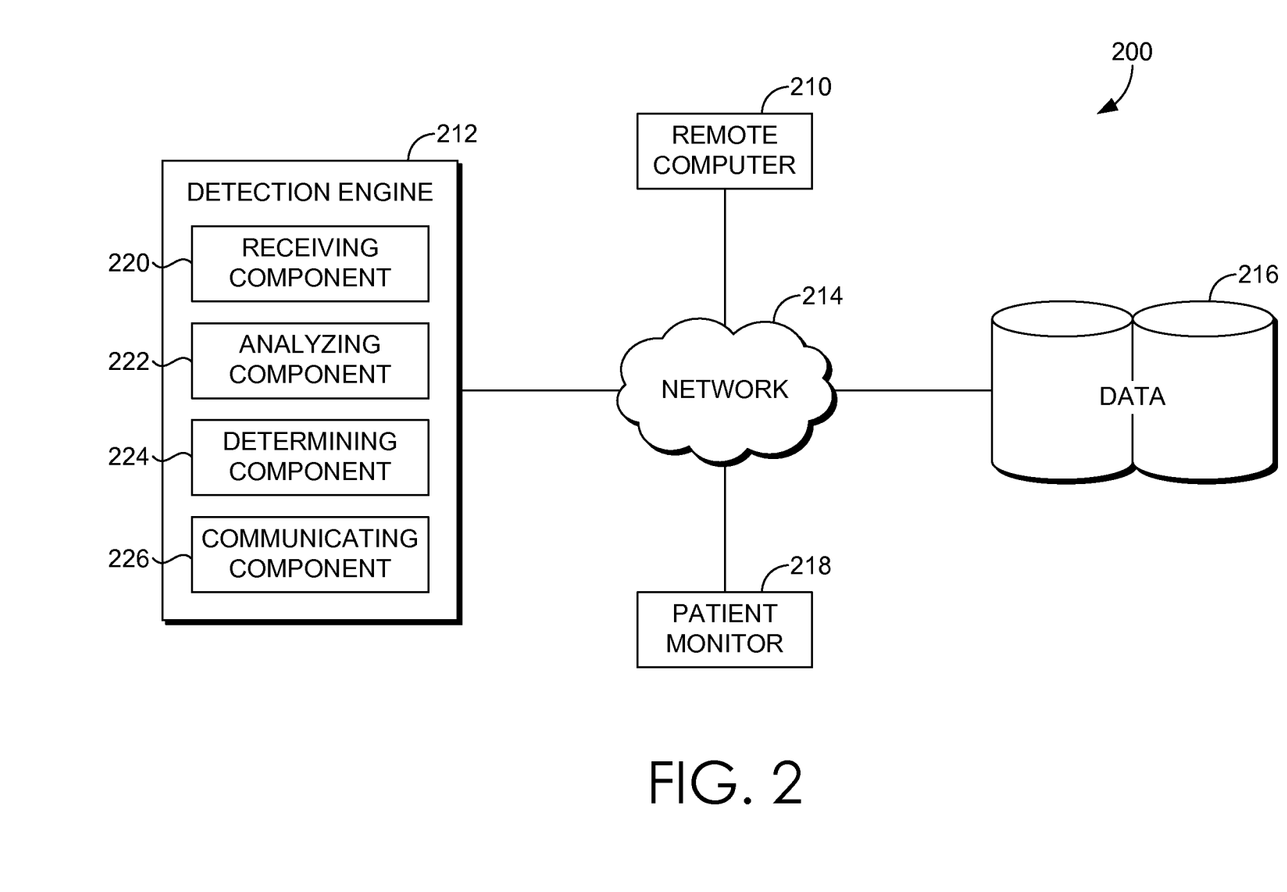
FIG. 2 is an exemplary system architecture suitable to implement embodiments of the present invention.

Turning to FIG. 2, an architectural framework 200 is shown for determining deterioration in left ventricular function and/or mitral valve function. This architectural framework 200 may operate, for instance, within the context of the exemplary medical information system 100 of FIG. 1. The system of FIG. 2 includes a remote computer 210, a detection engine 212, a network 214, a database 216, and a patient monitor 218. Other components not shown here may also be used to carry out aspects of the present invention. Further, several components shown in FIG. 2 may be combined into a single component although shown separately in FIG. 2. Alternatively, components, such as the database 216, although shown as a single component, may actually be two or more components.

The detection engine 212 includes a receiving component 220, an analyzing component 222, a determining component 224, and a communicating component 226. Each component of the detection engine 212 may assist in receiving, analyzing, storing, communicating, or the like, information relevant to generate a determination regarding deterioration in left ventricular function and/or mitral valve function. The detection engine 212 may be associated with a healthcare entity. Healthcare entities may include, but are not limited to, clinicians, hospitals, clinics, pharmacies, laboratories, and the like. Throughout this application, the term "user" is used interchangeably with healthcare entities and is not meant to limit the scope of the present invention in any way.

During monitoring of the deterioration of a particular patient's left ventricular function and/or mitral valve function, data is received by the receiving component 220. The receiving component 220 is configured to receive medical monitoring requests from a user. For example, a user of remote computer 210 may periodically request medical monitoring data from detection engine 212. Such a request may be repeated at regular intervals over a plurality of timepoints. As such, requests for monitoring data may be continuous over time. In embodiments, a single medical monitoring request may initiate the subsequent, continuous retrieval of data from the detection engine 212.

Receiving component 220 is further configured to receive patient data, such as periodically receiving patient data from patient monitor 218. Patient monitor 218 may be any type of patient monitor configured to collect transbrachial electrical impedance velocimetry data and/or arterial blood pressure data, such as the apparatus disclosed in U.S. Pat. No. 7,261, 697 (issued Aug. 28, 2007) entitled "Apparatus for Determination of Stroke Volume Using the Brachial Artery." For example, patient monitor 218 may monitor blood flow through a patient's brachial artery using electrical signals. In embodiments, patient monitor 218 includes separate sensors to detect and/or collect transbrachial electrical impedance velocimetry data and arterial blood pressure data. For example, a separate blood pressure sensor may be used to collect blood pressure data from the patient, while a brachial artery sensor may be used to detect blood flow. As such, patient monitor 218 may include a single sensor or multiple sensors. Further, data received from a transbrachial electrical impedance sensor may be used to provide an impedance timeseries, while data received from blood pressure sensor may be used to provide a blood pressure timeseries.

In some embodiments, patient monitor 218 operates on a smart phone running one or more application programs or "apps" for receiving the monitored or user-sensor information, conditioning the data or calculating results, and communicating the data. For example, in an embodiment, detection engine 212 comprises one or more apps running on a smart phone. Furthermore, in smart-phone embodiments, the phone's communication equipment may be used for communicating the data or results to a backend, for example, such as a health care provider or decision-support knowledge agent. These embodiments of the invention including patient monitor 218 may use other communication features of the smart phone such as Bluetooth, Wi-Fi, ZigBee or other low-rate wireless personal area network platforms or wireless communication technologies, to communicate with one or more sensors positioned on a user for collecting transbrachial electrical impedance velocimetry data and/or arterial blood pressure data, and in some embodiments, to communicate with a base station or user computer. Additional details relating to these embodiments may be found in U.S. patent application Ser. No. 12/982,625, which is herein incorporated by reference in its entirety.

In embodiments, receiving component 220 receives serial transbrachial impedance velocimetry data and serial arterial pressure waveform data from a particular patient's patient monitor 218 at a plurality of timepoints. For example, patient data may be continuously communicated over a plurality of timepoints to receiving component 220 by patient monitor 218, which results in constant patient monitoring. Additionally, at each timepoint, data may include one or more intervals of data observed during early systole and/or late systole using an echocardiograph. As discussed later with reference to FIG. 3, data retrieved during the early systole may provide an indication of left ventricular function, while data retrieved during late systole may provide an indication of mitral valve function. In embodiments, data from a single timepoint may include data from multiple intervals of the cardiac cycle, such as intervals during both early and late systole.

Once receiving component 220 receives patient data, analyzing component 222 is configured to determine a statistical copula between the second derivative of square-root-transformed patient-calibrated electrical transbrachial impedance velocimetry waveform timeseries $d^2 sqrt(Z(t)/Z_0)/dt^2$ and the first derivative of arterial blood pressure waveform timeseries dP/dt. For the timeseries "$d^2 sqrt(Z(t)/_{Z0})/d^{t2}$," "Z" represents the electrical impedance of blood flow measured by a patient monitor, "$sqrt Z(t)/_{Z0}$" represents the normalized form of impedance Z, and "$d^2 sqrt(Z(t)/_{Z0})/d^{t2}$" represents the second derivative of impedance (i.e. the acceleration). The timeseries "dP/dt" represents the rate of change in blood pressure "P" with respect to time "t."

In embodiments, copulas may be used to model multivariate non-normal longitudinal data, such as the copula determination described in U.S. Patent Application 61/391,121 filed Oct. 8, 2010, entitled "PREDICTING NEAR-TERM DETERIORATION OF HOSPITAL PATIENTS." As will be understood by one of skill in the art, a statistical copula may be used to determine a mathematical relationship between two or more variables. As further understood by one of skill in the art, a "square-root-transformed" timeseries refers to taking the square root of each value of the raw variables in the timeseries.

A "patient-calibrated" timeseries refers to adjusting the gain of the impedance sensor and amplifier, and signal acquisition circuit, for the baseline impedance $Z_0$ that characterizes a variety of factors with respect to the particular patient. For example, a timeseries may be calibrated with respect to the electrical impedance of the sensor's contact with a particular patient's skin, the geometry and muscle/fat composition of the tissue between the skin and the interior brachial artery, the geometry of the patient's brachial artery, the electrolyte composition of the patient's blood plasma, and other factors.

Raw values of received patient data may be modified by analyzing component 222. In embodiments, raw values of data may be modified so as to prevent "tied" values by adding and/or subtracting small fractional values from vector elements prior to determining a statistical copula with the received data. For example, a fractional random value less than 0.1 may be added or subtracted from each vector element before forming a bivariate copula of vectors.

Analyzing component 222 is further configured to determine a statistical norm for a particular patient. In embodiments, the statistical norm provides an indication of the particular patient's pattern of transbrachial impedance velocimetry data and arterial pressure waveform data. For example, a statistical norm may be determined based on serial transbrachial impedance velocimetry data and serial arterial pressure waveform data received at a plurality of timepoints. In embodiments, determining a statistical norm includes establishing a time-averaged baseline characterization of the impedance timeseries and/or the blood pressure timeseries over a statistically representative interval of time, which may be for example a minimum threshold of time or number of heart beats. As will be understood, any number of methods for calculation, and any number of time intervals, may be used to determine a statistical norm based on transbrachial impedance velocimetry data and/or arterial pressure waveform data.

A statistical norm determination may take into consideration other factors affecting the particular patient. For example, analyzing component 222 may determine a statistical norm for a particular patient that incorporates additional factors such as the particular patient's surgical history, or a recent medical episode that the patient encountered.

Receiving component 220 also receives a current data value for the patient. In embodiments, the current data value is used to determine the particular patient's current condition with respect to left ventricular function and/or mitral valve function. As such, the data may include transbrachial impedance velocimetry data and arterial pressure waveform data. The current data value may include data collected during multiple intervals of the systolic phase of the cardiac cycle. In embodiments, current data is received from the early systole phase and the late systole phase of the particular patient's cardiac cycle.

Based on the data received by receiving component 220 and analyzed by analyzing component 222, determining component 224 makes a determination regarding the extent of deterioration of a particular patient's left ventricular function and/or mitral valve function. In embodiments, a determination regarding a patient's current level of left ventricular function and/or mitral valve function may be based on comparing the patient's statistical norm with the patient's current level of deterioration in left ventricular function and/or deterioration in mitral valve function. In embodiments, determining component 224 makes a determination of deterioration in left ventricular function and/or mitral valve function using the statistical copulas determined by analyzing component 222. As such, determining component 224 interprets the copula analysis that characterizes the interdependency between the second derivative of square-root-transformed patient-calibrated transbrachial electrical impedance velocimetry waveform timeseries $d^2 sqrt(Z(t)/Z_0)/dt^2$ and the first derivative of arterial blood pressure waveform timeseries dP/dt at multiple intervals during the systolic phase of the patient's cardiac cycle.

In embodiments, the extent of deterioration in left ventricular function is determined by determining component 224 based on a statistical copula between the second derivative of square-root-transformed patient-calibrated transbrachial electrical impedance velocimetry waveform timeseries $d^2 sqrt(Z(t)/Z_0)/dt^2$ and the first derivative of arterial blood pressure waveform timeseries dP/dt during a first and second interval. Additionally, determining component 224 may identify a significant deterioration in left ventricular function based on the statistical copula between $d^2 sqrt(Z(t)/Z_0)/dt^2$ and dP/dt during the first and second intervals displaying a bivariate dependency and being well-fit by an extreme value distribution. Such a determination of left ventricular function may be made at each timepoint in a plurality of timepoints of received data.

In a further embodiment, the extent of deterioration in mitral valve function is determined by determining component 224 based on a statistical copula between the second derivative of square-root-transformed patient-calibrated transbrachial electrical impedance velocimetry waveform timeseries $d^2 sqrt(Z(t)/Z_0)/dt^2$ and the first derivative of arterial blood pressure waveform timeseries dP/dt during a third interval. Additionally, determining component 224 may identify a significant deterioration in mitral valve function based on the statistical copula between $d^2 sqrt(Z(t)/Z_0)/dt^2$ and dP/dt during the third interval displaying a bivariate dependency and being well-fit by an extreme value distribution. Such a determination of mitral valve function may be made at each timepoint in a plurality of timepoints of received data.

Communicating component 226 communicates the patient's left ventricular function status and/or mitral valve function status, as determined by the determining component 224. For example, during constant monitoring of the patient, communicating component 226 may communicate that the patient is experiencing a significant deterioration in left ventricular function, as determined by the determining component 224. In another example, the communicating component 226 may communicate that the patient is experiencing a significant deterioration in mitral valve function, as determined by the determining component 224. As such, communicating component 226 may generate a report indicating the status of the patient's left ventricular function and/or mitral valve function. In embodiments, data received by the receiving component 220 and analyzed by the analyzing component 222 may be continuously communicated by communicating component 226, regardless of whether a determination has been made that there is a significant deterioration in left ventricular function or mitral valve function. For example, communicating component 226 may provide data that indicates no change in a patient's left ventricular function or mitral valve function status.

Figure 3:
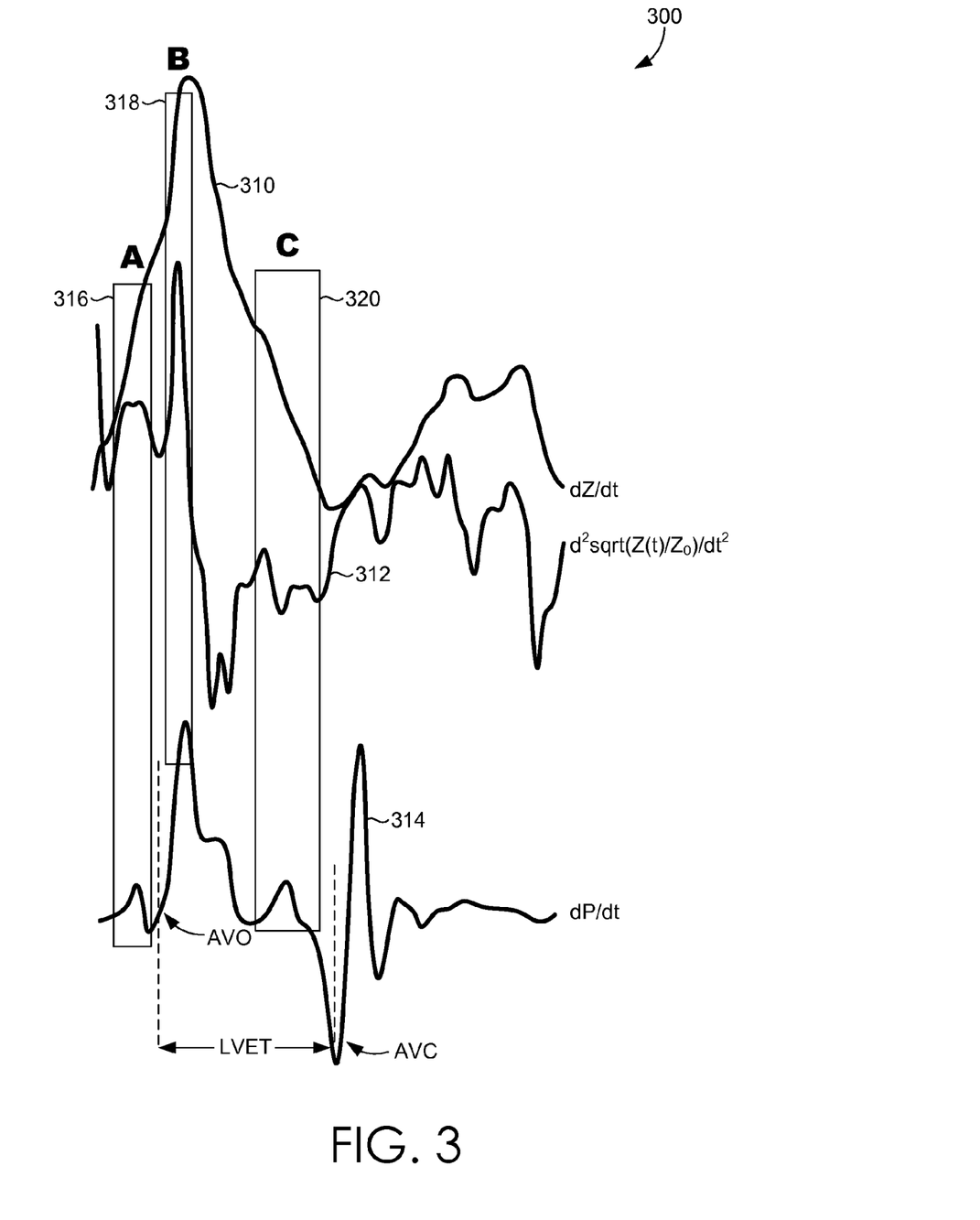
FIG. 3 depicts an exemplary display of received patient data.

Turning to FIG. 3, an exemplary display 300 of received patient data includes the display of electrocardiographic (ECG) waveform data indicating the first derivative of the impedance signal "Z" as "dZ/dt" 310, the second derivative of the impedance waveform timeseries "$d^2 sqrt(Z(t)/Z_0)/dt^2$" 312, and the pressure waveform timeseries "dP/dt" 314. Display 300 also identifies intervals of the systolic phase during which a copula analysis may be conducted by determining component 224. During each patient heartbeat, data may be identified at particular intervals during the systolic phase of the cardiac cycle, as identified using ECG waveform data and pressure waveform data. For example, display 300 identifies early systole intervals A 316 and B 318, and late systole interval C 320. As shown in FIG. 3, a first interval may be referenced as the ascending slope of the brachial curve between the onset of systole and the first shoulder (area "A" 316). A second interval may be identified on the ascending slope of the brachial curve between the first shoulder and the second shoulder (area "B" 318). A third interval may be identified on the descending slope of the curve between the second shoulder and the aortic valve closure (area "C" 320).

In embodiments, data identified in early systole intervals A 316 and B 318 provides an indication of LVD, while data identified in late systole interval C 320 provides an indication of MR. As such, a copula analysis may be conducted at intervals A 316 and B 318 to determine whether a patient is suffering from a recent deterioration in left ventricular function. In making such a determination, if the statistical copula between $d^2 sqrt(Z(t)/Z_0)/dt^2$ 312 and dP/dt 314 at intervals A 316 and B 318 displays a bivariate dependency and is well-fit by an extreme-value distribution, such as a Gumbel distribution, then a determination may be made that there has been a recent deterioration in the patient's left ventricular function. As will be understood by one of skill in the art, displaying a bivariate dependency generally refers to the copula between two variables, and data that is "well-fit" by an analytic distribution generally refers to the deviations between an empirical and a model distribution being small by one or more measures of "goodness-of-fit." Additionally, any number of extreme-value distributions, or types of distributions, may be used to analyze the statistical copula. It should be understood that a Gumbel distribution is only one example of a type of extreme-value distribution, and is not limiting in any sense.

Additionally, a copula analysis may be conducted at interval C 320 to determine whether a patient is suffering from a recent deterioration in mitral valve function. In making such a determination, if the statistical copula between $d^2sqrt(Z(t)/Z_0)/dt^2$ 312 and dP/dt 314 at intervals A 316 and B 318 displays a bivariate dependency and is well-fit by an extreme-value distribution, then a determination may be made that there has been a recent deterioration in the patient's mitral valve function.

Figure 4:
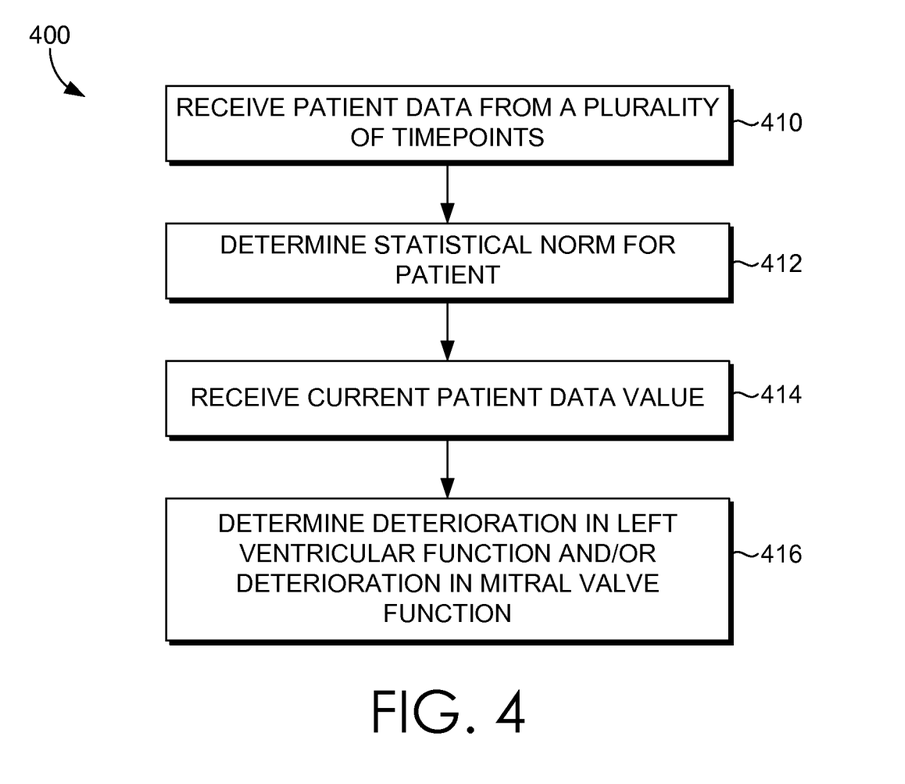
FIG. 4 is a flow diagram illustrating a first exemplary method for determining deterioration in left ventricular function and/or deterioration in mitral valve function.

An exemplary flow diagram illustrating a first exemplary method 400 for determining deterioration in left ventricular function and/or deterioration in mitral valve function is provided in FIG. 4. At block 410, patient data is received at a plurality of timepoints. Such patient data may include transbrachial impedance velocimetry data and arterial pressure waveform data collected from a particular patient. In embodiments, the received current data value may include data collected at a plurality of timepoints, and the data collected at each timepoint may include an indication for multiple intervals during the systolic phase of the cardiac cycle. Based on the received patient data, a statistical norm is determined for the patient at block 412. At block 414, current patient data value is received. At block 416, a determination is made regarding deterioration in left ventricular function and/or deterioration in mitral valve function. In embodiments, such a determination is based on the received patient data, the determined statistical norm, and the current patient data value.

Figure 5:
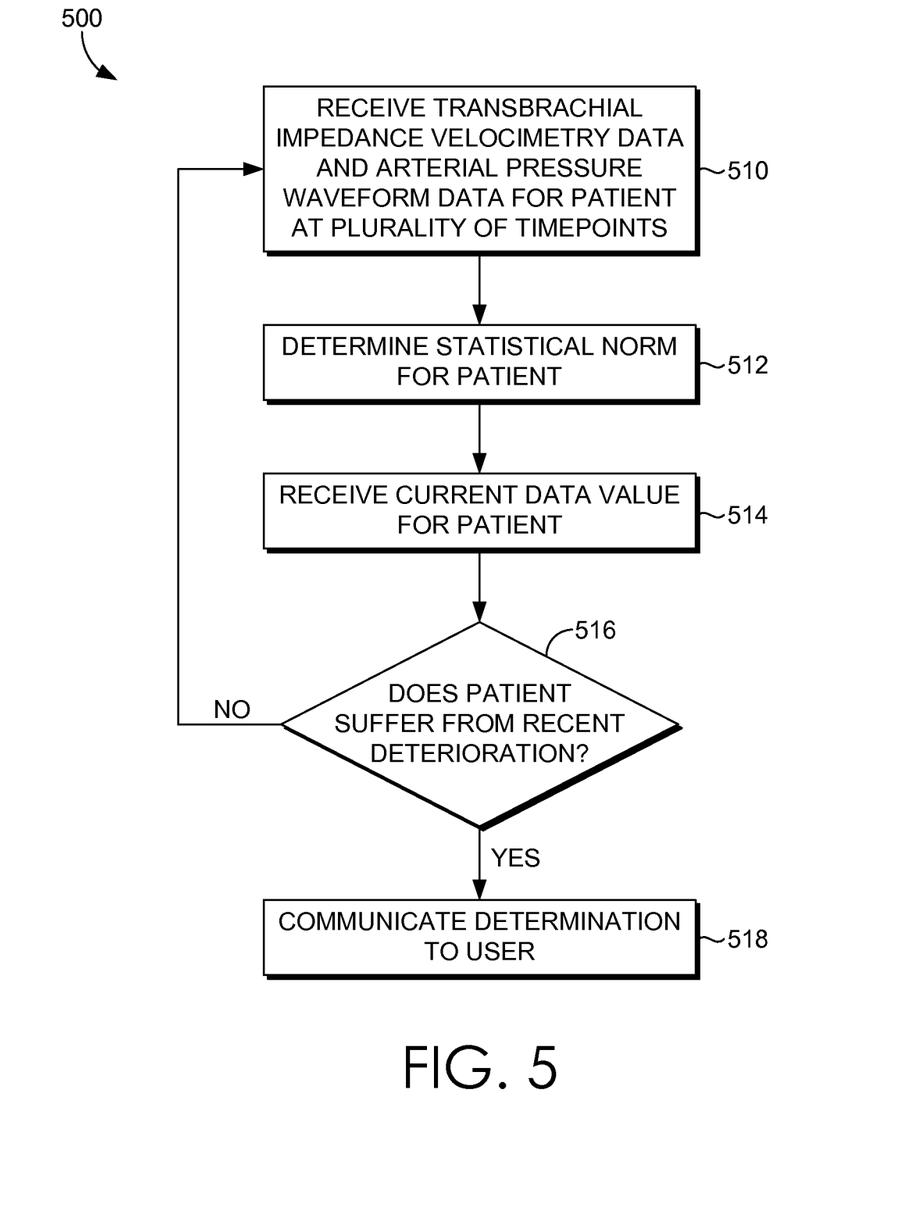
FIG. 5 is a flow diagram illustrating a second exemplary method for determining deterioration in left ventricular function and/or deterioration in mitral valve function.

With reference finally to FIG. 5, a flow diagram illustrating a second exemplary method for determining deterioration in left ventricular function and/or deterioration in mitral valve function is provided. At block 510, transbrachial impedance velocimetry data and arterial pressure waveform data for a patient are received at a plurality of timepoints. At block 512, a statistical norm is determined for the patient. At block 514, a current data value for the patient is received. A determination is made at block 516 as to whether the patient suffers from a recent deterioration in one or both of left ventricular function and mitral valve function. If a determination is made that the patient does not suffer from a recent deterioration in one or both of left ventricular function and mitral valve function, then the flow diagram returns to block 510, and additional patient data is received. If a determination is made that the patient does suffer from a recent deterioration in one or both of left ventricular function and mitral valve function, the determination is communicated to a user at block 518.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. One or more tangible computer storage devices storing computer-useable instructions that, when executed by one or more computing devices, cause the one or more computing devices to perform a method for classifying one or both of left ventricular function and mitral valve function, the method comprising:
   receiving data from a particular patient at a plurality of timepoints, wherein the data comprises transbrachial impedance velocimetry data collected from the patient at the plurality of timepoints and arterial pressure waveform data collected from the patient at the plurality of timepoints;
   determining an extent of deterioration at each of the plurality of timepoints of one or both of left ventricular function and mitral valve function based on the transbrachial impedance velocimetry data and the arterial pressure waveform data, the determining an extent of deterioration comprising determining a statistical copula between a second derivative of square-root-transformed patient-calibrated transbrachial electrical impedance velocimetry waveform timeseries $d^2sqrt(Z(t)/Z_0)/dt^2$ and a first derivative of arterial blood pressure waveform timeseries dP/dt during a first and second interval at each of the plurality of timepoints;
   determining a statistical norm for the particular patient based on the determined extent of deterioration;
   receiving a current data value from the patient at a current timepoint, wherein the current data value comprises transbrachial impedance velocimetry data collected from the patient at the current timepoint and arterial pressure waveform data collected from the patient at the current timepoint;
   determining whether the patient suffers from one or both of a recent deterioration in left ventricular function and a recent deterioration in mitral valve function, wherein determining whether the patient suffers from a recent deterioration is based on the statistical norm for the patient and the current data value; and
   generating a report indicating whether the patient suffers from one or both of a recent deterioration in left ventricular function and a recent deterioration in mitral valve function.

2. The one or more storage devices of claim 1, wherein receiving data comprises receiving one or more items of data from a monitor associated with a brachial artery of the patient.

3. The one or more storage devices of claim 1, wherein receiving data comprises receiving serial transbrachial impedance velocimetry data and serial arterial pressure waveform data.

4. The one or more storage devices of claim 1, wherein determining an extent of deterioration of left ventricular function comprises determining whether the statistical copula between $d^2sqrt(Z(t)/Z_0)/dt^2$ and dP/dt during the first and second intervals displays a bivariate dependency and is well-fit by an extreme value distribution.

5. The one or more storage devices of claim 1, wherein determining an extent of deterioration at each of the plurality of timepoints of mitral valve function comprises determining a statistical copula between a second derivative of square-root-transformed patient-calibrated transbrachial electrical impedance velocimetry waveform timeseries $d^2sqrt(Z(t)/Z_0)/$ $dt^2$ and a first derivative of arterial blood pressure waveform timeseries dP/dt during a third interval at each of the plurality of timepoints.

6. The one or more storage devices of claim 5, wherein determining an extent of deterioration of mitral valve function comprises determining whether the statistical copula between $d^2\text{sqrt}(Z(t)/Z_0)/dt^2$ and dP/dt during the third interval displays a bivariate dependency and is well-fit by an extreme value distribution.

7. The one or more storage devices of claim 1, wherein determining a statistical norm for the particular patient based on the determined extent of deterioration comprises establishing a time-averaged baseline characterization of the impedance timeseries and the blood pressure timeseries over a statistically representative interval of time greater than 500 beats.

8. The one or more storage devices of claim 1, wherein determining whether the patient suffers from a recent deterioration in left ventricular function comprises determining a statistical copula between a second derivative of square-root-transformed patient-calibrated transbrachial electrical impedance velocimetry waveform timeseries $d^2\text{sqrt}(Z(t)/Z_0)/dt^2$ and a first derivative of arterial blood pressure waveform timeseries dP/dt during a first and second interval at the current timepoint.

9. The one or more storage devices of claim 8, wherein determining whether the patient suffers from a recent deterioration in left ventricular function comprises determining whether the statistical copula between $d^2\text{sqrt}(Z(t)/Z_0)/dt^2$ and dP/dt during the first and second intervals at the current timepoint displays a bivariate dependency and is well-fit by an extreme value distribution.

10. The one or more storage devices of claim 9, wherein determining whether the patient suffers from a recent deterioration in left ventricular function comprises comparing the statistical copula during the first and second intervals at the current timepoint with the statistical norm for the patient.

11. The one or more storage devices of claim 1, wherein determining whether the patient suffers from a recent deterioration in mitral valve function comprises determining a statistical copula between a second derivative of square-root-transformed patient-calibrated transbrachial electrical impedance velocimetry waveform timeseries $d^2\text{sqrt}(Z(t)/Z_0)/dt^2$ and a first derivative of arterial blood pressure waveform timeseries dP/dt during a third interval at the current timepoint.

12. The one or more storage devices of claim 11, wherein determining whether the patient suffers from a recent deterioration in mitral valve function comprises determining whether the statistical copula between $d^2\text{sqrt}(Z(t)/Z_0)/dt^2$ and dP/dt during the third interval at the current timepoint displays a bivariate dependency and is well-fit by an extreme value distribution.

13. The one or more storage devices of claim 12, wherein determining whether the patient suffers from a recent deterioration in mitral valve function comprises comparing the statistical copula during the third interval at the current timepoint with the statistical norm for the patient.

14. The one or more storage devices of claim 1, wherein the method further comprises communicating the determination of whether the patient suffers from one or both of a recent deterioration in left ventricular function and a recent deterioration in mitral valve function to a user.

15. A method for classifying one or both of left ventricular function and mitral valve function, the method comprising:
receiving medical monitoring data from a particular patient, the medical monitoring data comprising transbrachial impedance velocimetry data and arterial pressure waveform data, wherein the medical monitoring data is received at a plurality of timepoints;
determining a statistical norm for the particular patient based on the medical monitoring data, the determining a statistical norm for the particular patient comprising determining a statistical copula between a second derivative of square-root-transformed patient-calibrated transbrachial electrical impedance velocimetry waveform timeseries $d^2\text{sqrt}(Z(t)/Zo)/dt^2$ and a first derivative of arterial blood pressure waveform timeseries dP/dt during two or more intervals at each of the plurality of timepoints;
receiving a current data value from the particular patient, the current data value comprising transbrachial impedance velocimetry data and arterial pressure waveform data;
based on the determined statistical norm and the received current data value, determining whether the patient suffers from one or both of a recent deterioration in left ventricular function and a recent deterioration in mitral valve function; and
generating a report indicating whether the patient suffers from one or both of a recent deterioration in left ventricular function and a recent deterioration in mitral valve function,
wherein the method is performed by one or more computing devices.

16. The method of claim 15, wherein determining a statistical copula comprises determining whether the statistical copula between $d^2\text{sqrt}(Z(t)/Z_0)/dt^2$ and dP/dt during two or more intervals displays a bivariate dependency and is well-fit by an extreme value distribution.

17. One or more tangible computer storage devices storing computer-useable instructions that, when executed by one or more computing devices, cause the one or more computing devices to perform a method for classifying left ventricular function and mitral valve function, the method comprising:
receiving data from a particular patient at a plurality of timepoints, wherein the data comprises transbrachial impedance velocimetry data collected from the patient at the plurality of timepoints and arterial pressure waveform data collected from the patient at the plurality of timepoints;
determining a statistical copula between a second derivative of square-root-transformed patient-calibrated transbrachial electrical impedance velocimetry waveform timeseries $d^2\text{sqrt}(Z(t)/Z_0)/dt^2$ and a first derivative of arterial blood pressure waveform timeseries dP/dt during a first and second interval at each of the plurality of timepoints;
determining an extent of deterioration at each of the plurality of timepoints of left ventricular function based on the statistical copula determined during the first and second intervals;
determining a statistical copula between a second derivative of square-root-transformed patient-calibrated transbrachial electrical impedance velocimetry waveform timeseries $d^2\text{sqrt}(Z(t)/Z_0)/dt^2$ and a first derivative of arterial blood pressure waveform timeseries dP/dt during a third interval at each of the plurality of timepoints;
determining an extent of deterioration at each of the plurality of timepoints of mitral valve function based on the statistical copula determined during the third interval;
determining a statistical norm for the particular patient based on the determined extent of deterioration of left ventricular function and the determined extent of deterioration of mitral valve function;

receiving a current data value from the patient at a current timepoint, wherein the current data value comprises transbrachial impedance velocimetry data collected from the patient at the current timepoint and arterial pressure waveform data collected from the patient at the current timepoint;

determining a statistical copula between a second derivative of square-root-transformed patient-calibrated transbrachial electrical impedance velocimetry waveform timeseries $d^2\text{sqrt}(Z(t)/Z_0)/dt^2$ and a first derivative of arterial blood pressure waveform timeseries dP/dt during a first and second interval at the current timepoint;

determining an extent of deterioration at the current timepoint of left ventricular function based on the statistical copula determined during the first and second intervals;

determining a statistical copula between a second derivative of square-root-transformed patient-calibrated transbrachial electrical impedance velocimetry waveform timeseries $d^2\text{sqrt}(Z(t)/Z_0)/dt^2$ and a first derivative of arterial blood pressure waveform timeseries dP/dt during a third interval at the current timepoint;

determining an extent of deterioration at the current timepoint of mitral valve function based on the statistical copula determined during the third interval;

determining whether the patient suffers from one or both of a recent deterioration in left ventricular function and a recent deterioration in mitral valve function, wherein determining whether the patient suffers from a recent deterioration is based on the statistical norm, the determined extent of deterioration of left ventricular function at the current timepoint, and the determined extent of deterioration of mitral valve function at the current timepoint; and generating a report indicating whether the patient suffers from one or both of a recent deterioration in left ventricular function and a recent deterioration in mitral valve function.

18. The one or more storage devices of claim 17, wherein determining whether the patient suffers from one or both of a recent deterioration in left ventricular function and a recent deterioration in mitral valve function comprises one or more of:

determining that the statistical copula between $d^2\text{sqrt}(Z(t)/Z_0)/dt^2$ and dP/dt during the first and second intervals at the current timepoint displays a bivariate dependency and is well-fit by an extreme value distribution; and determining that the statistical copula between $d^2\text{sqrt}(Z(t)/Z_0)/dt^2$ and dP/dt during the third interval at the current timepoint displays a bivariate dependency and is well-fit by an extreme value distribution.

* * * * *